(12) United States Patent
Frank et al.

(10) Patent No.: US 8,999,310 B1
(45) Date of Patent: Apr. 7, 2015

(54) RAPID PERMANENT HAIR SETTING FORMULATION, SYSTEM AND METHOD

(71) Applicant: Chuckles, Inc., Manchester, NH (US)

(72) Inventors: Charles P. Frank, Bedford, NH (US); Joseph J. Crudden, Hudson, NH (US)

(73) Assignee: Chuckles, Inc., Manchester, NH (US)

( * ) Notice: Subject to any disclaimer, the term of this patent is extended or adjusted under 35 U.S.C. 154(b) by 0 days.

(21) Appl. No.: 14/327,595

(22) Filed: Jul. 10, 2014

Related U.S. Application Data

(60) Provisional application No. 61/845,099, filed on Jul. 11, 2013.

(51) Int. Cl.
| | |
|---|---|
| *A61K 8/64* | (2006.01) |
| *A61Q 5/04* | (2006.01) |
| *A61Q 5/12* | (2006.01) |
| *A45D 7/06* | (2006.01) |
| *A61K 8/895* | (2006.01) |
| *A61K 8/44* | (2006.01) |

(52) U.S. Cl.
CPC ............. *A61K 8/895* (2013.01); *A61K 8/447* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 7,547,454 B2 | 6/2009 | Gupta | |
| 7,988,954 B2 | 8/2011 | Chandra et al. | |
| 2003/0059382 A1 | 3/2003 | Brandt et al. | |
| 2011/0180093 A1 | 7/2011 | Verboom et al. | |
| 2013/0295030 A1* | 11/2013 | Yamazaki | 424/70.2 |

FOREIGN PATENT DOCUMENTS

WO    2012/027369 A2    3/2012

OTHER PUBLICATIONS

Wacker Silicones, BELSIL P 1101, Silicone Polyvinyl Acetates, technical data sheet, 2 pages, date of last alteration: Apr. 11, 2012.
Wacker Silicones, BELSIL ADM 8301 E, Amino-Functional Sllicone, technical data sheet, 2 pages, date of last alteration: Mar. 19, 2013.

* cited by examiner

*Primary Examiner* — Jeffrey T Palenik
(74) *Attorney, Agent, or Firm* — Nields, Lemack & Frame, LLC

(57) ABSTRACT

Keratinous fiber treatment formulations and methods of providing a long lasting set in keratinous fibers such as hair by applying a polymer system to the hair which provides a stable set to the hair which will last at least until the hair is thoroughly washed. The set is made more permanent by incorporating a reducing agent such as L-cysteine into the polymer system and allowing the system to air oxidize over time or optionally applying a second chemical oxidizing system to the treated hair which will accelerate the oxidation process and the setting rate of the hair.

4 Claims, No Drawings

RAPID PERMANENT HAIR SETTING FORMULATION, SYSTEM AND METHOD

This application claims priority of U.S. Provisional Application Ser. No. 61/845,099 filed Jul. 11, 2013, the disclosure of which is incorporated herein by reference.

BACKGROUND OF INVENTION

Hair styling, shaping or setting compositions are well known for use in styling the hair, including retaining a particular shape, curl or "wave" in the hair (e.g., a "perm"). Hair styling compositions also may be used to straighten naturally curly hair, or frizzy hair. These typically include a chemical treatment that includes breaking disulfide bonds in hair keratin through chemical reduction, followed by stretching the hair, and then oxidizing the air to restore the disulfide bonds.

Hair is composed of keratin, which becomes elastic, tending to return to its original state after having been bent. In order to create a permanent wave, the side chains of keratin are broken to temporarily remove the elasticity of hair, and then are recombined to set the hair in the desired configuration.

Conventional hair perm systems include a first agent that acts as a reducing agent to reduce the cysteine bonds in the keratin, and a second agent to oxidize the keratin to recombine the side chains previously broken by the reduction action of the first agent to wave and straighten hair.

A cold wave can be achieved in this manner, i.e., by applying a reducing agent such as thioglycolate to the hair to break sulfur bonds. The hair is next formed to the desired shape. The hair is then treated with an oxidizing agent such as a peroxide to reform the disulfide links in the hair. When the disulfide links re-form, they lock the hair in the set conformation.

However, this process is time consuming and expensive, requiring a session of at least 90 minute in the salon. This type of a permanent wave or "perm" may last up to six weeks, until the hair grows out.

Temporary waves or temporary setting of hair can be achieved with polymer or protein systems. In these systems, the polymer solution is applied to the hair and the hair is heated with a flat iron or a hair drier to about 400° F. This process removes moisture from the hair and causes the hair to relax by breaking the hydrogen bonds in the hair, which hold a certain type of structure. When the hair and applied polymer cools, the polymer sets and locks in the structure in which the hair is arranged. This type of temporary wave may last for a few days, but when the hair is washed, the polymer, which is water soluble, dissolves away and the water breaks the hydrogen bonds and allows the hair to return to its original conformation, and the set or wave is lost.

It would be desirable to provide a hair styling system, composition and method that allows for much faster hair straightening or hair wave or curl formation, and maintains the altered conformation for a long period of time.

SUMMARY

The problems of the prior art have been addressed by the embodiments disclosed herein, which relate to keratinous fiber treatment formulations and methods of providing a long lasting set in keratinous fibers such as hair by applying a polymer system to the hair which provides a stable set to the hair which will last at least until the hair is thoroughly washed. The set is made more permanent by incorporating a reducing agent such as L-cysteine into the polymer system and allowing the system to air oxidize over time or optionally applying a second chemical oxidizing system to the treated hair which will accelerate the oxidation process and the setting rate of the hair. When the temporary set polymer is removed from the hair, the bonds broken by L-cysteine and reformed by the oxidation process will result in the hair holding a permanent set conferred on the hair by the temporary setting process achieved by the polymer system.

The embodiments disclosed herein allow a permanent set to be achieved simply and rapidly. A conventional cold wave takes at least 90 minutes in the salon. The embodiments disclosed herein allow a permanent wave (or straightening) to be achieved in about 15 minutes, thereby reducing skin or scalp irritation and providing a more efficient and cost-effective process.

DETAILED DESCRIPTION

The embodiments disclosed herein are applicable to keratinous fibers, including but not limited to human and animal hair. Such hair includes but is not limited to body hair, head hair, wool and fur.

Suitable polymers for use in the embodiments disclosed herein include BELSIL® P1101, manufactured by Wacker Chemie, which is a crotonic acid/vinyl $C_{8-12}$ isoalkyl esters/VA/bis-vinyldimethicone crosspolymer. This polymer has excellent resistance to ambient moisture and can hold a set for up to at least a few days, or until the hair is washed multiple times. Other suitable polymers include BELSIL® ADM 8301 E (Wacker Chemie AG), which is Amodimethicone/Morpholinomethyl Silsesquioxane, Trideceth-5.

In accordance with certain embodiments, the hair setting is made more permanent by incorporating in the formulation an effective amount of L-cysteine or an acceptable salt thereof. Suitable salts of L-cysteine include ammonium salts, quaternary ammonium salts and amine salts (for example, monoethanolamine, diethanolamine and triethanolamine salts). An effective amount is an amount sufficient to achieve an acceptable persistent set, that lasts at least two weeks, preferably at least three weeks, and as long as about 2 months. Suitable amounts of cysteine include from about 0.1 to 25 percent, Preferably between 0.5 and 5%, most preferably about 2-3% of the formulation. In certain embodiments, the polymer/cysteine polymer system is neutralized to about pH 8 in aqueous solution with a suitable base, such as ammonium hydroxide to produce ammonium cysteine solution, AMP or alkanolamines. An ammonium cysteine solution of about 50% solids is suitable for addition to the polymer solution to give a cysteine content of about 2%. In certain embodiments, the cysteine is neutralized so that it is above pH 7, preferably about 8.2 prior to being mixed with the polymer system. Suitable neutralizing agents include ammonia and aminomethyl propanol.

When cysteine dissolved in water comes into contact with oxygen from the air, it can dimerize to Cystine by oxidation:

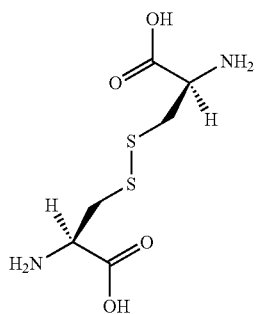 [SMILES: N[C@@H](CSSC[C@H](N)C(=O)O)C(=O)O]

Cystine is inactive as a reducing agent and of low solubility in water. This problem can be overcome by adding an antioxidant to the system such as ascorbic acid, erythorbic acid, sodium sulfite, sodium metabisulfite, Butyl hydroxyl anisole etc. Suitable amounts include about 0.3 to about 2.5% based on the formulation, preferably about 1%.

In accordance with certain embodiments, one or more additional oxidizers can be added to expedite the process. Suitable oxidizing agents include peroxide and peroxide producing systems, such as sodium percarbonate that dissociates in water to produce hydrogen peroxide. Sodium perborate or sodium perborate monohydrate also may be used. Sodium perborate can be used with bleach activators such as tetraacetylethylenediamine and sodium nonanoyloxybenzene-sulfonate. These materials produce a surface active bleach which is drawn to the surface of fibers and is thus efficient. Other peroxide systems, such as hydrogen peroxide solution, that are typically used in hair dyeing or setting may be suitable.

The hair treatment formulations of the embodiments disclosed herein may further contain other compatible ingredients, which are generally used in this technical field. Examples include surfactants, solvents, humectants, sensation improvers, oils, antiseptics, colorants, perfumes, stabilizers, suspending agents, appearance controllers, viscosity modifiers, anti-inflammatory agents, chelating agents, water, preservatives, thickeners, sunscreening agents, fragrances, moisturizers, softeners, anti-foaming agents, anti-dandruff agents, germicides, conditioners, etc.

When the polymer system is applied to the hair, the hair may be arranged by the application of heat from a suitable source, such as a flat iron, curling iron or blow dryer, into the desired conformation, to heat the polymer-coated hair. As the polymer cools, the conformation is locked in by the polymer. Disulfide bonds are broken by the reducing agent, locking the keratin into the conformation imposed on the system by the cooled polymer and rearranged hydrogen bonds. As time passes, for example about 24 hours, the sulfur-to-sulfur bonds reform by air oxidation. When sufficient S—S bonds form to hold the hair in the arranged conformation, a permanent wave is achieved.

The application of the formulation to the hair can be carried out by any suitable means, including spraying, combing and/or brushing, or dispensing the formulation from a container or housing, and spreading or working it through the hair. Suitable forms for the formulation include a cream, spray, lotion, mousse, or solution.

In certain embodiments, after the formulation is applied to the hair, hair washing should be avoided for one to two days, allowing the polymer system to retain the hair in place as air oxidation reforms the sulfur-to-sulfur bonds in the hair. In certain embodiments, if an auxiliary oxidizing agent is used as discussed above, rapid setting of the hair can be achieved and hair washing can occur sooner.

Once the polymer is washed from the hair, the permanent S—S bonds that have formed will hold the hair in a permanent configuration for a much longer period of time, spanning multiple weeks or months. This process makes it possible either to make the hair wavy or to relax it, uncurl it or straighten it.

In certain embodiments, the setting cysteine and polymer formulation may be applied from a flat iron which dispenses liquids. For example, a flat iron having dual dispense capabilities could be used so that the reducing agent is applied from one dispenser and the oxidizing agent sequentially from a second dispenser. Applying cysteine to break the sulfur bonds with the application of heat from a flat iron, for example, the oxidation process may proceed very quickly.

One suitable formulation is shown below in Table 1:

TABLE 1

| Phase | INCI | Trade Name | Conc. [%] |
|---|---|---|---|
| A | Aminomethyl Propanol | AMP 95 (Angus Chemical Company) | 0.31 |
| | Crotonic AcidNinyl C8-12 Isoalkyl EstersNA/Bis-Vinyldimethicone Crosspolymer | BELSILO P1101 (Wacker Chemie AG) | 12.00 |
| B | Deionized Water | Water | 81.39 |
| C | Propylene Glycol, Diazolidinyl Urea, Methylparaben & Propylparaben | Germaben II (ISP, Inc) | 0.30 |
| D | Ammonium Cysteine 50% solution | (pH 8) | 6.00 |
| Total | | | 100.00 |

Adjust pH to about 8 to 8.2 with citric acid and/or ammonium hydroxide solution.

Other formulations of the system such as pomades, gels and mousses can be produced which will allow the rapid permanent set to be achieved in a similar manner.

Other suitable formulations are shown in the Tables below:

TABLE 2

| Trade Name | INCI | Conc. [%] |
|---|---|---|
| A | | |
| DI Water | Aqua | 85.59 |
| Tween 20 (Croda) | Polysorbate-20 | 0.60 |
| B | | |
| Incroquat CTC-30 LQ (Croda) | Cetrimonium Chloride | 0.70 |
| Glycerin(Acme Hardesty) | Glycerin | 0.20 |
| Germaben II (ISP, Inc) | Propylene Glycol, Diazolidinyl Urea, Methylparaben & Propylparaben | 0.20 |
| C | | |
| BELSIL ® ADM 8301 E (Wacker Chemie AG) | Amodimethicone/ Morpholinomethyl Silsesquioxane, Trideceth-5, Glycerin | 5.71 |
| D | | |
| Ajidew NL-50 (Ajinomto Co. Inc) | Sodium Pyrrolidone Carboxylate | 2.00 |
| E | | |
| Cysteine (50% aq) | Cysteine | 5.00 |
| Total | | 100.00 |

Adjust pH to 8-8.2 with citric acid solution or ammonium hydroxide solution.

TABLE 3

| INCI | TradeName | Conc. [%] |
|---|---|---|
| A | | |
| Aqua (DI Water) | Water | 35.25 |
| Alcohol | Dent Ethanol +1% MEK | 10.00 |
| PEG-40 Hydrogenated Castor Oil | Cremophor RH 40 | 0.50 |
| B | | |
| Alcohol (and) Crotonic Acid/Vinyl C8-12 Isoalkyl Esters /VA/Bis-Vinyldimethicone Crosspolymer | BELSIL ® P1101 | 4.00 |

TABLE 3-continued

| INCI | TradeName | Conc. [%] |
|---|---|---|
| Aminomethyl Propanol | AMP 30%ig | 0.33 |
| C | | |
| Polyquaternium-4 | Celquat L200 | 0.40 |
| Aqua (DI Water) | Water | 25.00 |
| Cysteine (50% aq) | Cysteine | 5.00 |
| D | | |
| Amodimethicone/ | BELSIL ® ADM 8301E | 0.50 |
| Morpholinomethyl | Phenonip | 0.50 |
| Silsesquioxane Copolymer, | | |
| Trideceth-5, | | |
| Phenoxyethanol and | | |
| Methylparaben and | | |
| Ethylparaben and | | |
| Butylparaben | | |
| Propylparaben and | | |
| Isobutylparaben | | |
| Cocamidopropyl Betaine | Amphosol CA | 5.52 |
| E | | |
| Propane / Butane | Propan/Butan | 8.00 |
| Total | | 100.00 | pH 8.0 to 8.2 adjusted with citric acid or Ammonium hydroxide.

As used herein, the phrase "consisting essentially of" limits the scope of a claim to the specified materials or steps and those that do not materially affect the basic and novel characteristics of the claimed subject matter. The term permits the inclusion of substances which do not materially affect the basic and novel characteristics of the composition under consideration. Accordingly, the expressions "consists essentially of" or "consisting essentially of" mean that the recited embodiment, feature, component, etc. must be present and that other embodiments, features, components, etc., may be present provided the presence thereof does not materially affect the performance, character or effect of the recited embodiment, feature, component, etc. The presence of impurities or a small amount of a material that has no material effect on a composition is permitted. Also, the intentional inclusion of small amounts of one or more non-recited components that otherwise have no material effect on the character or performance of a composition is still included within the definition of "consisting essentially of". For example the use of additional polymers or the use of additional reducing agents would be considered to materially affect the basic and novel characteristics of the claimed subject matter. Similarly, additional method steps that add significant time to the application process would be considered to materially affect the basic and novel characteristics of the claimed subject matter.

EXAMPLE 1

One hundred grams of the resin system described in Table 1 is placed in a 200 ml beaker and agitated on a magnetic stirrer at medium speed. Six grams of a 50% solution of ammonium cysteine is gradually added with constant stirring. The ammonium cysteine easily dissolves in the polymer resin system leaving no precipitate or residue.

EXAMPLE 2

The formulation from Example 1 is placed in a pump sprayer for ease of application. It is applied to swatches of human hair using the spray bottle and a comb. A flat iron is used to apply heat to the coated hair, to a temperature of about 200° C. in order to drive off water and cause the temporary set.

The base polymer system works as described and provides a temporary robust set to the hair. As the set remains in the hair the S—S bonds broken by the heat and reducing agent are gradually reformed in the new conformation by air oxidation and a more permanent set is achieved. Conventional washing is not capable of breaking S—S bonds and reversing a permanent set.

EXAMPLE 3

The formulation shown in Table 1 was placed in a trigger spray bottle and applied to curly hair of a human subject. One half of the head was treated and the other half was left untreated.

The product was applied to individual swatches of hair, spraying from the bottle and combing in until the hair was saturated. A flat iron at 200° C. was used to straighten the hair. Heating the hair to this temperature drives off water and relaxes the hair. As the hair cools, the polymer system containing the L-cysteine reducing agent sets the hair temporarily. However, before the temporary set is lost the natural air oxidation of the sulfur linkages in the keratin reforms the S—S bonds in the hair and permanently sets the hair in the conformation in which it is being held.

The hair was washed after a few days and the hair remained straight on the treated side, in stark contrast to the untreated side, which remained highly curled. After three weeks and several washings, the straightened hair retained the set.

What is claimed is:

1. A keratinous fiber treatment formulation consisting essentially of a crotonic acid/vinyl $C_{8-12}$ isoalkyl esters/VA/bis-vinyldimethicone crosspolymer and an effective amount of a 50% ammonium cysteine solution having a pH ranging from about 8 to about 9.

2. A method of styling hair, comprising applying to said hair a formulation consisting essentially of a crotonic acid/vinyl $C_{8-12}$ isoalkyl esters/VA/bis-vinyldimethicone crosspolymer and an effective amount of L-cysteine or a salt thereof.

3. The method of claim 2, further comprising heating said hair to about 200° C.

4. The method of claim 2, wherein said hair is human hair.

* * * * *